US008652850B2

(12) United States Patent
Koide et al.

(10) Patent No.: US 8,652,850 B2
(45) Date of Patent: Feb. 18, 2014

(54) METHOD OF QUANTITATIVELY DETERMINING 8-ISOPROSTANE

(75) Inventors: Satoshi Koide, Itabashi-Ku (JP); Kenji Yokoyama, Hachioji (JP); Yoshio Suzuki, Hachioji (JP)

(73) Assignees: Tanita Corporation, Itabashi-Ku, Tokyo (JP); National Institute of Advanced Industrial Science and Technology, Chiyoda-Ku, Tokyo (JP)

( * ) Notice: Subject to any disclaimer, the term of this patent is extended or adjusted under 35 U.S.C. 154(b) by 191 days.

(21) Appl. No.: 13/364,822

(22) Filed: Feb. 2, 2012

(65) Prior Publication Data

US 2012/0220040 A1 Aug. 30, 2012

(30) Foreign Application Priority Data

Feb. 28, 2011 (JP) ................................. 2011-042816

(51) Int. Cl.
*G01N 21/64* (2006.01)

(52) U.S. Cl.
USPC ............................ 436/139; 436/164; 436/172

(58) Field of Classification Search
USPC .......................................... 436/139, 164, 172
See application file for complete search history.

(56) References Cited

U.S. PATENT DOCUMENTS 4,800,223 A 1/1989 Ohkura

FOREIGN PATENT DOCUMENTS

| JP | 3-291272 A | 12/1991 |
| JP | 2004-157119 A | 6/2004 |
| WO | WO 2008/065895 A1 | 6/2008 |

OTHER PUBLICATIONS

Lee, C-Y J. et al., "Measurement of F₂-Isoprostanes, Hydroxyeicosatetraenoic Products, and Oxysterols From a Single Plasma Sample", Free Radical Biology & Medicine 44, vol. 44, No. 7, pp. 1314-1322 (Apr. 1, 2008) XP-022797582.
Lee, C-Y J. et al., "Rapid Preparation of Human Urine and Plasma Samples for Analysis of F₂-Isoprostanes by Gas Chromatography-Mass Spectrometry", Biochemical and Biophysical Research Communications, vol. 320, No. 3, pp. 696-702 (Jul. 30, 2004) XP-004518006.
Konishi, M. et al., "Determination of Pivaloylcarnitine in Human Plasma and Urine by High-Performance Liquid Chromatography With Fluorescence Detection", Journal of Pharmaceutical Sciences, vol. 81, No. 10, pp. 1038-1041 (Oct. 1, 1992) XP-55027146.
Dahl, S.R. et al., "Detecting pM Concentrations of Prostaglandins in Cell Culture Supernatants by Capillary SCX-LC-MS/MS", Journal of Separation Science, vol. 31, No. 14, pp. 2627-2633 (Aug. 1, 2008) XP-55027157.
Kitano, S. et al., "Improved Method of Plasma 8-Isoprostane Measurement and Association Analyses With Habitual Drinking and Smoking", World Journal of Gastroenterology, vol. 12, No. 36, pp. 5846-5852 (Sep. 28, 2006) XP-55026400.
Basu, S., "Metabolism of 8-Iso-Prostaglandin $F_{2\alpha}$", FEBS Letters, vol. 428, No. 1-2, pp. 32-36 (May 22, 1998) XP-004257906.
Extended European Search Report dated May 29, 2012, issued in corresponding European Patent Application No. 12156124.5-1223. (11 pages).

*Primary Examiner* — Krishnan S Menon
*Assistant Examiner* — Dwan A Gerido
(74) *Attorney, Agent, or Firm* — Buchanan Ingersoll & Rooney PC

(57) ABSTRACT

A method of quantitatively determining 8-isoprostane is provided that includes fluorescently labeling 8-isoprostane with a quinoxalinone derivative in an excess amount relative to 8-isoprostane, separating a fluorescently labeled 8-isoprostane from a unreacted quinoxalinone derivative by contacting a reaction mixture containing the fluorescently labeled 8-isoprostane and the unreacted quinoxalinone derivative with a cation exchange support having a sulfonic acid or a sulfonate immobilized thereon, and quantitatively determining the fluorescently labeled 8-isoprostane that has been separated from the unreacted quinoxalinone derivative.

16 Claims, 4 Drawing Sheets

METHOD OF QUANTITATIVELY DETERMINING 8-ISOPROSTANE

This application is based on Japanese patent application No. 2011-042816, the content of which is incorporated hereinto by reference.

BACKGROUND

1. Technical Field

The present invention relates to a method of quantitatively determining 8-isoprostane.

2. Related Art 8-isoprostane is a prostaglandin-like compound formed by oxidation of phospholipid contained in cell membrane or lipoprotein by means of free radicals. Oxidative stress in vivo can be noninvasively evaluated by measuring 8-isoprostane contained in a biological sample such as urine or serum. A kit for measuring 8-isoprostane by an immunoassay is also commercially available.

Japanese Laid-Open Patent Publication No. 2004-157119 describes a technique related to an immunoassay for 8-isoprostane.

WO 2008/065895 describes a technique related to analysis of 8-isoprostane by an LC-MS/MS method.

SUMMARY

However, the precision for quantitative determination in a conventional method of analyzing 8-isoprostane is very low. The present inventors found the possibility of quantitative analysis by fluorescently labeling 8-isoprostane with a quinoxalinone derivative described in Japanese Laid-Open Patent Publication No. 3-291272. However, there is still room to improve the technique of Japanese Laid-Open Patent Publication No. 3-291272 in order to label in good yield a trace amount of 8-isoprostane contained in a biological sample such as urine and so on and increase the precision of quantitative analysis.

The present invention has been accomplished in light of the above-mentioned circumstances, and it is an object thereof to provide a technique that enables quantitative determination of 8-isoprostane to be carried out with good precision.

In one embodiment, there is provided a method of quantitatively determining 8-isoprostane, the method comprising fluorescently labeling 8-isoprostane with a quinoxalinone derivative in an excess amount relative to the amount by mole of 8-isoprostane, the quinoxalinone derivative which is represented by Formula (1) below, contacting a reaction mixture containing fluorescently labeled 8-isoprostane and an unreacted quinoxalinone derivative with a cation exchange support having a sulfonic acid or a sulfonate immobilized thereon to separate the fluorescently labeled 8-isoprostane from the unreacted quinoxalinone derivative, and quantitatively determining the fluorescently labeled 8-isoprostane separated from the unreacted quinoxalinone derivative.

In Formula (1), $R^1$, $R^2$, and $R^3$ are alkyl groups having 1 to 6 carbon atoms, and n is an integer of 0 to 6.

In another embodiment, there is provided a kit for quantitatively determining 8-isoprostane, the kit being used in the method of quantitatively determining 8-isoprostane.

In accordance with the present invention, 8-isoprostane is fluorescently labeled with a quinoxalinone derivative, and then the fluorescently labeled 8-isoprostane and the quinoxalinone derivative are separated using a cation exchange support. Therefore, it is possible to carry out labeling in good yield by the use of an excess amount of quinoxalinone derivative and to remove the excess amount of quinoxalinone derivative by adsorbing it on the cation exchange support even when a trace amount of 8-isoprostane is used. Accordingly, it becomes possible to carry out quantitative analysis of 8-isoprostane with good precision by quantitatively determining fluorescently labeled 8-isoprostane.

In accordance with the present invention, 8-isoprostane can be quantitatively determined with good precision.

BRIEF DESCRIPTION OF THE DRAWINGS

The above and other objects, advantages and features of the present invention will be more apparent from the following description of certain preferred embodiments taken in conjunction with the accompanying drawings.

DETAILED DESCRIPTION

The invention will be now described herein with reference to illustrative embodiments. Those skilled in the art will recognize that many alternative embodiments can be accomplished using the teachings of the present invention and that the invention is not limited to the embodiments illustrated for explanatory purposed.

In all the drawings, similar components are denoted by similar reference numerals and symbols, thus avoiding duplication of the explanation as appropriate.

First Embodiment

Figure 1:
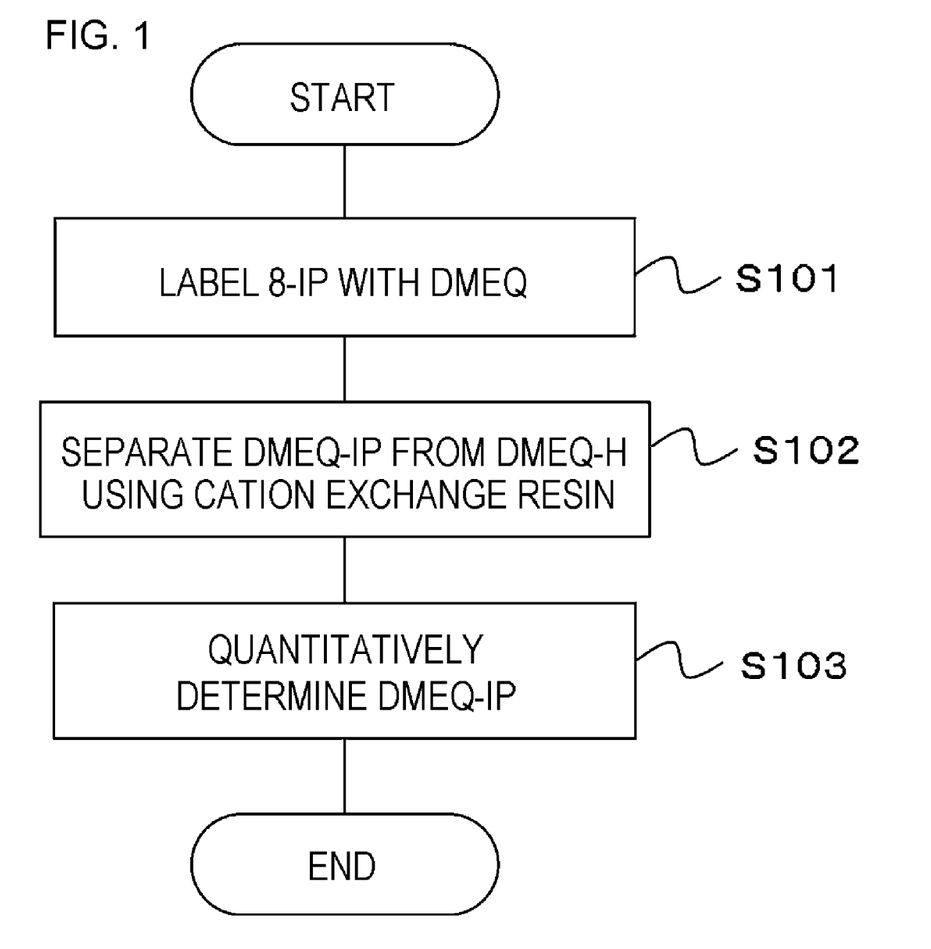
FIG. 1 shows a flowchart illustrating a method of quantitatively determining 8-isoprostane related to a first embodiment.

FIG. 1 is a flowchart showing a method of quantitatively determining 8-isoprostane (8-IP) of the present embodiment. The present embodiment includes a step (S101) of fluorescently labeling 8-IP with 1,2,3,4-tetrahydro-6,7-dimethoxy-1-methyl-2(1H)-oxoquinoxaline-3-propionic acid hydrazide (DMEQ-H, (a compound of Formula (1) above for which $R^1$, $R^2$, and $R^3$ are all methyl and n is 2)) in an excess amount relative to the amount by mole of 8-IP as a quinoxalinone derivative, a step (S102) of contacting a reaction mixture containing fluorescently labeled 8-isoprostane (DMEQ-IP) and an unreacted DMEQ-H with a cation exchange support having a sulfonic acid or a sulfonate immobilized thereon to separate DMEQ-IP from the unreacted DMEQ-H, and a step (S103) of quantitatively determining DMEQ-IP separated from the unreacted DMEQ-H. Each step is explained in detail below.

[S101: Step of Fluorescently Labeling 8-IP]

In step S101, DMEQ-IP is synthesized by reacting the carboxyl group of 8-IP and the hydrazide group of DMEQ to form an amide bond. The reaction conditions are not particularly limited, and it is preferable to carry out the reaction in a solvent in the presence of a base and an activating agent for activating a carboxylic acid. As the solvent, water, an alcohol, or an aprotic polar solvent is preferably used, and dimethylformamide is more preferably used. As the base, an aliphatic tertiary amine or a nitrogen-containing heterocyclic compound is preferable, and pyridine is more preferable. As the activating agent, a carbodiimide is preferable, dicyclohexylcarbodiimide (DCC), diisopropylcarbodiimide (DIC), or 1-ethyl-3-(3-dimethylaminopropyl)carbodiimide hydrochloride (EDC) is more preferable, and EDC is particularly preferable.

When the reaction is carried out in a solvent, the concentration of the 8-IP that is to be labeled is not particularly limited, and it may be 0.01 to 0.5 nmol/mL.

DMEQ is preferably used in an excess amount relative to 8-IP, and it is preferably used at least $2 \times 10^3$ times by mole relative to 8-IP, more preferably $5 \times 10^3$ times by mole, and particularly preferably $1 \times 10^5$ times by mole. There is no particular upper limit, but it may be no more than $2 \times 10^5$ times by mole.

When a base such as pyridine is used, it is preferably used at 50 to 1000 times by mole relative to DMEQ, and more preferably 100 to 500 times by mole.

When an activating agent such as water-soluble carbodiimide is used, it is preferably used in an excess amount relative to 8-IP, and it is preferably used at $1 \times 10^2$ to $5 \times 10^5$ times by mole relative to 8-IP, and more preferably $2 \times 10^3$ to $5 \times 10^4$ times by mole.

The reaction temperature may be no lower than room temperature (15° C. to 30° C.). In order to enhance the reaction efficiency it is preferable to heat to 50° C. to 90° C., and more preferably 60° C. to 80° C. The reaction time is not limited, and it may be 10 to 60 minutes.

The yield at which 8-IP is labeled under the above-mentioned reaction conditions may be 50% to 100%.

[S102: Step of Separating DMEQ-IP from DMEQ-H]

Any cation exchange support may be used in step S102 as long as a sulfonic acid or a sulfonate is immobilized thereon, and it is preferably one having an alkylbenzenesulfonic acid represented by Formula (2) below or a salt thereof immobilized thereon.

In Formula (2), m is 1 to 6 and $B_1$ is a resin substrate or silica gel.

Furthermore, as the cation exchange support represented by Formula (2), one having propylbenzenesulfonic acid, for which m is 3, or a salt thereof immobilized thereon is preferable. Moreover, in Formula (2), $B_1$ is for example silica gel or a resin substrate formed from a copolymer of styrene and divinylbenzene and so on, and silica gel is preferable. The amount of cation exchange support used is preferably such that the content (eq) of the sulfonic acid or sulfonate is 1 to 1000 times that of the DMEQ used in step S101.

A method of contacting a liquid containing DMEQ-IP and DMEQ-H with the cation exchange support is not particularly limited and may be a batch method or a column method, but the column method is suitable. When a sulfonate is used as the cation exchange support, the counterion for the sulfonate is preferably converted into sodium ion. The counterion for the sulfonate may be converted into sodium ion by contacting the cation exchange support with an aqueous solution of sodium hydroxide, brine, and so on. It is preferable for the cation exchange support to be equilibrated by means of sufficient water, alcohol, and predetermined buffer. A buffer that is adjusted so as to have a pH of 5.5 to 8.5, preferably 6.0 to 8.0, and more preferably 6.5 to 7.5, can be exemplified. In the present specification, the buffer is one in which a predetermined acid is dissolved in water and the type thereof may be selected as appropriate according to the pH. For example, an acetic acid buffer may be used for a pH range of 5.5 to 5.6, a citric acid buffer for a pH range of 5.5 to 6.2, a citric acid-phosphoric acid buffer for a pH range of 5.5 to 7.0, a phosphoric acid buffer for a pH range of 5.5 to 8.5, and a tris-phosphoric acid buffer for a pH range of 7.2 to 8.5. Furthermore, this buffer preferably contains 0 to 100 vol %, and preferably 10 to 80 vol %, of a water-soluble organic solvent (in particular ethanol). The pH in the present specification is that measured at 25° C.

In the case of the column method, a reaction mixture containing DMEQ-IP and an unreacted DMEQ-H is passed through a conditioned cation exchange support so that DMEQ-IP and DMEQ-H are retained on the cation exchange support. In this process, with regard to the reaction mixture, the reaction mixture may be diluted with a water-soluble organic solvent such as ethanol, a buffer, or a liquid mixture thereof.

Subsequently, anionic substances or nonionic substances that have not been captured by the cation exchange support are washed away by a washing liquid. As the washing liquid, one containing a water-soluble organic solvent and water as main components is preferable; as the water-soluble organic solvent ethanol, acetonitrile, methanol, and so on may be used, and the concentration thereof in the washing liquid may be 10 to 100 vol %, and preferably 30 to 100 vol %. The washing liquid preferably contains a buffer, and the pH of the buffer may be for example 5.5 to 8.5, preferably 6.0 to 8.0, and more preferably 6.5 to 7.5. A liquid mixture of ethanol and a phosphoric acid buffer is preferable, and it is preferable for ethanol to be contained in the washing liquid at 0 to 100 vol %, preferably 30 to 100 vol %, and more preferably 50 to 100 vol %. The amount of washing liquid may be 0.1 to 100 mL, preferably 0.1 to 50 mL, and more preferably 0.1 to 20 mL.

After washing, DMEQ-IP that has been retained on the cation exchange support is eluted from the cation exchange support using an eluent containing a water-soluble organic solvent and water as main components (S103). The eluent may contain a water-soluble organic solvent such as ethanol, acetonitrile, or methanol, and the concentration thereof in the eluent may be 10 to 100 vol %, and preferably 30 to 100 vol %. The eluent preferably contains a buffer, and the pH of the buffer may be 5.5 to 8.5, preferably 6.0 to 8.0, and more preferably 6.5 to 7.5. Furthermore, a liquid mixture of ethanol and a phosphoric acid buffer is more preferable, and it is more preferable for ethanol to be contained in the eluent at 0 to 100 vol %, preferably 30 to 100 vol %, and more preferably 50 to 100 vol %. 0.1 to 10 mL of the eluent is passed through, and the first approximately 0.2 to 0.3 mL of the eluent passed is collected. The amount of eluent and the amount of liquid collected can be increased/decreased according to the size of the support used, the amount of sample, and so on. In this way, DMEQ-IP is obtained. Since DMEQ-H has strong adsorptivity on the cation exchange resin, the liquid collected contains DMEQ-IP but does not contain DMEQ-H. In this way, DMEQ-IP can be separated from DMEQ-H.

[S103: Step of Quantitatively Determining DMEQ-IP]

DMEQ-IP is quantitatively determined by a high-performance liquid chromatographic (HPLC) method using the DMEQ-IP obtained in step S102. Solvent in the collected liquid collected from the cation exchange resin in S102 may be removed as appropriate before HPLC. In this HPLC method, a reverse phase column chromatographic method employing a reverse phase column may be used. The column is preferably heated, and is preferably heated to 40° C. to 60° C. The mobile phase is preferably a liquid mixture of an alcohol and a buffer. Specifically, a liquid mixture of methanol and an acetic acid buffer is preferable used. The pH of the mobile phase is preferably weakly acidic, and a pH of 4 to 6 is more preferable. It may be isocratic or gradient. From the viewpoint of improving the precision of quantitative determination, it is preferably isocratic. It is preferable that the fluorescence excitation spectrum has a maximum at 367 nm and the fluorescence emission spectrum has a maximum of 445 nm. It is possible to quantitatively determine DMEQ-IP injected into the HPLC equipment by measuring the fluorescence intensity of DMEQ-IP.

With regard to the precision with which the fluorescence intensity of DMEQ-IP is quantitatively determined, the coefficient of variation can be no more than 20%. Furthermore, when in the range of 1 to 1000 pmol, the peak height and the amount of DMEQ-IP are proportional to each other, and the correlation coefficient can be 0.99 or more.

In this way, the amount of 8-isoprostane used in S101 may be determined based on the amount of DMEQ-IP determined. The amount by mole of DMEQ-IP obtained in S103 may be defined as the amount by mole of 8-IP that is used for labeling, or the amount by mole of 8-IP used may be calculated while taking into consideration the yield of labeling. In such a method of quantitatively determining 8-IP of the present embodiment, 8-isoprostane is fluorescently labeled with DMEQ, and then DMEQ-IP is separated from DMEQ using the cation exchange support. Therefore, it is possible to carry out labeling in good yield using an excess amount of DMEQ, and to remove the excess amount of DMEQ by adsorbing it on the cation exchange support even when 8-isoprostane in a trace amount such as no more than 100 pmol, furthermore no more than 50 pmol is used. Accordingly, 8-isoprostane can be quantitatively analyzed with good precision by quantitatively determining DMEQ-IP.

Any kit for quantitatively determining 8-isoprostane in the method of quantitatively determining 8-isoprostane related to the above-mentioned present embodiment includes DMEQ-H, a cation exchange support having a sulfonic acid immobilized thereon, a predetermined washing liquid, and an eluent. The DMEQ-His preferably a dimethylformamide solution, the cation exchange support is preferably a cation exchange support in which propylbenzenesulfonic acid or a salt thereof is immobilized on silica gel, and the washing liquid and the eluent are preferably liquid mixtures of ethanol and a phosphoric acid buffer. This eluent may be in a form such that the ethanol and the phosphoric acid buffer are separately packaged and preparation thereof is carried out by the user. It more preferably contains a base such as pyridine and a carbodiimide such as EDC, or a solution thereof. Such a kit includes written instructions in which the method of quantitatively determining 8-isoprostane related to the present embodiment is described.

Second Embodiment

Figure 2:
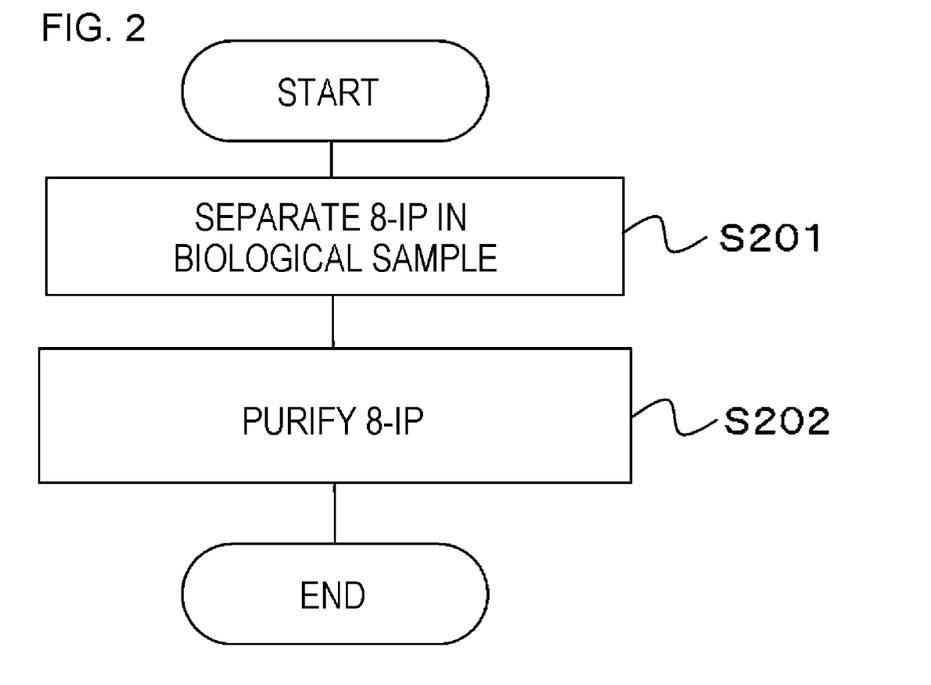
FIG. 2 shows a flowchart illustrating a method of quantitatively determining 8-isoprostane related to a second embodiment.

FIG. 2 is a flowchart showing part of a method of quantitatively determining 8-isoprostane (8-IP) of the present embodiment. The present embodiment is a method of quantitatively determining 8-IP in a biological sample. The present embodiment includes a step (S201) of separating 8-IP in a biological sample and a step (S202) of purifying the separated 8-IP using an anion exchange support, and steps S101, S102, and S103 explained in the first embodiment are carried out using the separated and purified 8-IP. In the present embodiment, only points that are different from the first embodiment are explained.

[S201: Step of Separating 8-IP in Biological Sample]

As the biological sample prepared in S201, a body fluid such as urine, blood, or saliva can be exemplified. A example that urine is used as the sample is explained below. The amount of urine sampled may be 0.5 to 50 mL, preferably 1.0 to 10 mL, and more preferably 1.5 to 5.0 mL from the viewpoint of reliably carrying out measurement. The original urine that has been sampled may be used as it is. Furthermore, urine may be diluted with a predetermined buffer or water. In this case, another additive such as a chelating agent, for example, EDTA (ethylenediaminetetraacetic acid) may be added. Although it is preferable that urine is concentrated immediately after sampling, it may be done a few hours to a few days thereafter.

The reverse phase support used in S201 is preferably formed from a material having a straight-chain hydrocarbon group having 1 to 30 carbon atoms as a functional group; it is more preferably a straight-chain hydrocarbon group having 8 to 22 carbon atoms, and even more preferably a straight-chain hydrocarbon group having 10 to 20 carbon atoms from the viewpoint of more efficiently treating 8-isoprostane in the biological sample. The amount of reverse phase support may be 0.1 to 10 times as much as the weight of urine.

Specifically, silica gel having an octadecylsilyl (ODS) group chemically bonded thereto can be exemplified as a material for the reverse phase support. Regarding the manner in which a silylating agent is bonded in the silica gel having an octadecylsilyl (ODS) group chemically bonded thereto, the silylating agent may be bonded to silanol groups of the silica gel at 1:1. In other word, a monomeric bonding manner may be employed. In this way, it is possible to prevent a reverse phase packing from getting excessively hydrophobic. From the viewpoint of having more desirable hydrophobicity, the reverse phase support may have a support surface carbon (C) content of 18% or less as an element ratio, and preferably 15% or less.

The reverse phase support preferably contains small particles having 0.5 to 10 μm of an equivalent circle diameter measured by a flow particle image analyzer at 1 to 20 cumulative % as a particle number. Furthermore, it may further contain large particles having 20 to 100 μm of an equivalent circle diameter measured by the above-mentioned analyzer at 65 to 99 cumulative % as a particle number, and preferably 78 to 99 cumulative %. In this way, even when a contaminant that has slightly different attributes such as molecular weight and properties from 8-IP is contained, separation thereof can be carried out simply and reliably. This reason is thought to be that formulating particles having different particle sizes at a specific ratio allows small particles to enter between large particles, and to maximize the surface area of the support per unit volume, and thereby improving the retentivity for 8-IP.

From the viewpoint of efficiently carrying out separation of 8-IP, the proportion as a particle number of small particles having 0.5 to 10 μm of an equivalent circle diameter measured by a flow particle image analyzer may be 4 to 19 cumulative %, preferably 4 to 13 cumulative %, and more preferably 6 to 13 cumulative %. Moreover, the proportion as a particle number of large particles having 20 to 100 μm of an equivalent circle diameter measured by the above-mentioned analyzer may be 68 to 95 cumulative %, preferably 78 to 93 cumulative %, and more preferably 85 to 91 cumulative %.

The flow particle image analyzer is a device for acquiring an image of particles during passage by irradiating with light such as stroboscopic light a flow cell in which a sample containing particles as a measurement target is flowing, and calculating a parameter showing particle shape such as equivalent circle diameter by image analysis. Since particles that have collapsed to an oval shape are present in practice, the equivalent circle diameter is defined as the diameter of a sphere that is assumed to have the same projection area as the particle projection area of the particle that is actually measured. Specific examples of the flow particle image analyzer include the FPIA-3000 manufactured by Sysmex Corporation.

The reverse phase support may contain larger medium particles having 35 to 60 μm of a particle size measured by a sedimentation method, and smaller medium particles having 10 to 30 μm of a particle size measured by a Coulter method. The ratio by weight of the larger medium particles having 35 to 60 μm of the particle size and the smaller medium particles having 10 to 30 μm of the particle size may be in the range of 80:20 to 95:5 (the larger medium particles:the smaller medium particle). In this way, the recovery rate of 8-IP can be further improved. From the viewpoint of improving the balance between recovery rate for 8-IP and separation time, the ratio by weight of the larger medium particles having 35 to 60 μm of the particle size and the smaller medium particles having 10 to 30 μm of the particle size is preferably 90:10 (the larger medium particles:the smaller medium particle).

The biological sample is preferably contacted with a reverse phase support that has been fully conditioned in advance with water and an alcohol, and more preferably conditioned with ethanol and pure water (and further with a buffer). Furthermore, conditioning may be carried out using a buffer having a pH of 5.5 to 8.5. The method of contacting the biological sample with the reverse phase support is not particularly limited and may be a batch method or a column method. From the viewpoint of 8-isoprostane being efficiently concentrated, the column method is suitable. In step S201, a combination of silica gel having an octadecylsilyl (ODS) group chemically bonded thereto and a phosphoric acid buffer-ethanol liquid mixture may be used as a combination of the reverse phase support and a mobile phase.

Subsequently, a predetermined buffer and so on is passed through the reverse phase support as a washing liquid, and substances that have not been captured by the reverse phase support is washed away. As the washing liquid in S202, one containing a water-soluble organic solvent and water as main components may be used. The water-soluble organic solvent such as ethanol, acetonitrile, methanol may be used, and the concentration thereof in the washing liquid may be 10 to 100 vol %, and preferably 30 to 100 vol %. The washing liquid in S202 may be used a buffer which is adjusted to pH of 5.5 to 8.5, preferably 6.0 to 8.0, and more preferably 6.5 to 7.5. A liquid mixture of ethanol and a phosphoric acid buffer is even more preferable. It is more preferable that the washing liquid may contain ethanol at 0 to 70 vol %, preferably 0 to 50 vol %, and more preferably 0 to 30 vol %. The amount of washing liquid may be set at 1 to 100 mL, preferably 1 to 50 mL, and more preferably 1 to 20 mL. Furthermore, it is preferable that the content of ethanol is gradually increased. It is more preferable that washing is carried out with 0 to 20 vol % content ethanol/phosphoric acid buffer, then with 20 to 40 vol % content ethanol/phosphoric acid buffer, and then with 40 to 60 vol % content ethanol/phosphoric acid buffer.

After washing, 8-IP retained on the reverse phase support is eluted from the reverse phase support with an eluent. The eluent containing a water-soluble organic solvent and water as main components may be used. The water-soluble organic solvent such as ethanol, acetonitrile, or methanol may be used, and the concentration thereof in the second eluent may be set at 10 to 100 vol %, and preferably 30 to 100 vol %. The eluent may preferably contain a buffer having pH of 5.5 to 8.5, preferably 6.0 to 8.0, and more preferably 6.5 to 7.5. Furthermore, the eluent is preferably a liquid mixture of ethanol and a phosphoric acid buffer, and it is preferable that ethanol may be contained in the eluent at 10 to 100 vol %, preferably 30 to 100 vol %, and more preferably 50 to 100 vol %. For example, 0.5 to 10 mL of the second eluent is passed, and about 1 mL eluting over 0.7 to 1.7 mL is collected. The amount of eluent and the amount of liquid collected can be increased or decreased according to the size of the reverse phase support used, the amount of sample, and so on. In this way, 8-isoprostane can be separated from a biological sample.

[S202: Step of Purifying 8-IP]

In step S202, 8-IP that has been separated from a biological sample is purified using an anion exchange support. With regard to the anion exchange support, a weak anion exchange support having a primary or secondary amine immobilized thereon. An anion exchange support having an aromatic or aliphatic quaternary ammonium immobilized thereon, and so on may be used, but an anion exchange support having a quaternary ammonium salt immobilized thereon is preferable. As the quaternary ammonium salt, a tetraalkylammonium salt represented by Formula (3) is preferable.

(3)

In Formula (3), $R^4$, $R^5$, and $R^6$ are alkyl groups having 1 to 6 carbon atoms, p is 1 to 5, $B_2$ is a resin substrate or silica gel, and $X^-$ is a chloride ion.

In particular, the anion exchange support immobilized a trimethylammonium propyl group that is $R^4$, $R^5$, and $R^6$ are methyl groups and p is 3 in Formula (3) is preferable. In Formula (3), $B_2$ is silica gel or a resin substrate formed from a copolymer of styrene and divinylbenzene and so on, and it is preferably silica gel. The amount of anion exchange support used is preferably such that the content (eq) of the quaternary ammonium salt is 1 to 100,000 times the number of moles of 8-IP contained in the liquid sample. For example, it may be set at 0.01 to 1 eq relative to 1 mL of urine when 8-IP in urine is purified.

The method of contacting 8-IP with the anion exchange support is not particularly limited, and may be a batch method or a column method, but the column method is suitable. The counterion for the quaternary ammonium salt of the anion exchange support is preferably converted into chloride ion. The counterion for the quaternary ammonium salt may be converted into chloride ion by contacting the anion exchange support with hydrochloric acid, brine, and so on. Subsequently, it is equilibrated with sufficient water, alcohol, and predetermined buffer. A buffer having the pH thereof adjusted to 5.5 to 8.5, preferably 6.0 to 8.0, and more preferably 6.5 to 7.5 can be exemplified as the buffer. This buffer preferably contains a water-soluble organic solvent (particularly ethanol) at 0 to 100 vol %, and preferably 10 to 80 vol %.

In the case of the column method, a liquid sample is made to flow through a conditioned anion exchange support so that 8-IP is retained on the anion exchange support, and cationic substances or nonionic substances that have not been captured by the anion exchange support are then washed away by means of a washing liquid. The washing liquid may contain a water-soluble organic solvent and water as main components. The water-soluble organic solvent such as ethanol, acetonitrile, or methanol may be used, and the concentration thereof in the washing liquid may be set at 10 to 100 vol %, and preferably 30 to 100 vol %. The washing liquid also may preferably contain a buffer, and a buffer having a pH of for example 5.5 to 8.5, preferably 6.0 to 8.0, and more preferably 6.5 to 7.5 may be used. Furthermore, a liquid mixture of ethanol and a phosphoric acid buffer is preferable, and ethanol may be contained in the washing liquid at 0 to 100 vol %, preferably 30 to 100 vol %. The amount of washing liquid may be set at 1 to 100 mL, preferably 1 to 50 mL, and more preferably 1 to 20 mL.

After washing, 8-IP retained on the anion exchange support is eluted from the anion exchange support using a first eluent containing a water-soluble organic solvent and water as main components. The eluent may contain a water-soluble organic solvent such as ethanol, acetonitrile, or methanol, and the concentration thereof in the eluent may be set at 10 to 100 vol %, and preferably 30 to 100 vol %. The eluent may contain a buffer and the pH of the buffer may be 5.5 to 8.5, preferably 6.0 to 8.0, and more preferably 6.5 to 7.5. Furthermore, a liquid mixture of ethanol and a phosphoric acid buffer is more preferable, and it is more preferable that ethanol is contained in the first eluent at 0 to 100 vol %, preferably 30 to 100 vol %, and more preferably 50 to 100 vol %. For example, 0.1 to 10 mL of the first eluent is passed, and about 1 mL eluting over 1.5 to 2.5 mL is collected. The amount of eluent and the amount of liquid collected can be increased or decreased according to the size of the support used, the amount of sample, and so on. In this way, purification of 8-IP can be carried out.

8-IP is concentrated in the liquid thus collected, and this may be subjected to labeling of the 8-IP (S101). The solvent in the liquid collected may be removed as appropriate before analysis of 8-IP.

A kit for quantitatively determining 8-IP contained in a biological sample, used in the above-mentioned method of quantitatively determining 8-IP related to the present embodiment may further include a reverse phase support and an eluent containing a water-soluble organic solvent and water as main components in addition to those described in the first embodiment. This eluent is preferably a liquid mixture of ethanol and a phosphoric acid buffer. This eluent may also be in a form such that the ethanol and the phosphoric acid buffer are separately packaged and preparation thereof is carried out by the user. Furthermore, it may further include an anion exchange support having a quaternary ammonium salt immobilized thereon, a washing liquid, and an eluent; as the anion exchange support an ion exchange support in which a trimethylammoniumpropyl group is immobilized on silica gel is preferable, and as the washing liquid and the eluent a liquid mixture of ethanol and a phosphoric acid buffer is preferable. This eluent may also be in a form such that the ethanol and the phosphoric acid buffer are separately packaged and preparation thereof is carried out by the user. Such a kit includes written instructions in which the method of purifying 8-isoprostane related to the present embodiment is described.

Embodiments of the present invention are explained above by reference to the attached drawings, but they are only illustrations of the present invention, and various configurations other than those described above may be employed.

For example, in the above-mentioned embodiments, a case in which DMEQ is used as a quinoxalinone derivative is explained, but the technique described in the embodiment of the present invention may be employed as long as it is a quinoxalinone derivative represented by Formula (1). For example, 1,2,3,4-tetrahydro-6,7-dimethoxy-1-methyl-2 (1H)-oxoquinoxaline-3-carboxy hydrazide (a compound for which in Formula (1) $R^1$, $R^2$, and $R^3$ are all methyl and n is 0) may be used.

Furthermore, in the second embodiment, a method of separating 8-isoprostane from a biological sample and a method of purifying the separated 8-isoprostane are explained. However, 8-isoprostane that has been separated from a biological sample may be subjected to steps S101 to S103 without purification. Moreover, purification of 8-isoprostane of step S202 may be carried out using chemically synthesized 8-isoprostane or 8-isoprostane that has been separated from a biological sample by a method other than step S201, and steps S101 to S103 may be carried out.

In the second embodiment, a example in which 8-isoprostane in urine is purified is explained, but in a case in which 8-isoprostane in serum is purified, a concentration operation may be carried out prior to quantitative determination because the normal value of 8-isoprostane is on the order of 1/100 of the value in urine. For example, a 100 times concentration operation involving setting a serum sample in a heat block at 50° C. and removing solvent under a flow of nitrogen may be added. In this way, a peak due to 8-isoprostane in serum can be observed clearly when steps S101 to 103 are carried out and fluorescently labeled 8-isoprostane is analyzed by HPLC.

EXAMPLES

Example 1

A 10 ng/mL (30 pmol/mL) 8-isoprostane solution was prepared by dissolving 2 ng of an authentic sample (Cayman)

of 8-isoprostane in 0.2 mL of 8% (v/v) ethanol-containing 10 mM phosphoric acid buffer (pH 7.0). 150 µL thereof was taken and mixed with 75 µL of Reagent I ($5 \times 10^4$ times by mole relative to 8-isoprostane), 60 µL of Reagent II (500 times by mole relative to DMEQ-H), and 15 µL of Reagent III ($2.5 \times 10^5$ times by mole relative to 8-isoprostane), and a reaction was carried out at 70° C. for 20 minutes. Subsequently, cooling was carried out by means of running water for 10 minutes. An SCX manufactured by Varian (ion exchange capacity: 0.8 meq/g, amount of packing 0.25 g, column size 4 mL, column shape syringe type, polypropylene) was prepared by conditioning with ethanol and pure water in that order, and the cooled reaction liquid was introduced. After washing with 0.2 mL of 8% (v/v) ethanol-containing 10 mM phosphoric acid buffer (pH 7.0), a fraction obtained by passing 0.2 mL of 8% (v/v) ethanol-containing 10 mM phosphoric acid buffer (pH 7.0) was collected as an analytical sample for 8-isoprostane. The analytical sample thus collected was injected into an HPLC as it was.

<Reagents>

Reagent I: 10 mM 1,2,3,4-tetrahydro-6,7-dimethoxy-1-methyl-2(1H)-oxoquinoxaline-3-propionic acid hydrazide (DMEQ-H)/dimethylformamide Reagent II: 10% (v/v) pyridine/20 mM hydrochloric acid-containing ethanol Reagent III: 0.5 M 1-ethyl-3-(3-dimethylaminopropyl)carbodiimide hydrochloride/purified water <HPLC Conditions>

| | |
|---|---|
| Flow rate | 1.2 mL/min |
| Column oven | 50° C. |
| Analysis column | Divelosil ODS MG5 (250 mm, φ4.6 mm) |
| Amount injected | 10 µL |
| Fluorescence detector | Ex: 367 nm, Em: 445 nm |
| Mobile phase | Methanol: 25 mM acetic acid/sodium acetate (pH 4.5) = 55:45 (isocratic) |

Example 2

A reverse phase column packing was prepared by uniformly mixing ODS-AQ manufactured by YMC having particle sizes of 50 µm and 20 µm at a ratio by weight of 50 µm:20 µm=90:10 as a reverse phase support. The 50 µm particle size was measured by a sedimentation method and the 20 µm particle size was measured by a Coulter method. The reverse phase column packing thus prepared contained small particles having 0.5 to 10 µm of an equivalent circle diameter measured by a flow particle image analyzer (FPIA-3000 manufactured by Sysmex Corporation) of at 10 cumulative % as a particle number and large particles having 20 to 100 µm of an equivalent circle diameter measured by the above analyzer at 90 cumulative % as a particle number. A reverse phase column charged with 800 mg of this packing was prepared, and passed ethanol and water in that order for conditioning.

A total of 2 mL of sample prepared by mixing 1.4 mL of urine (National Institute of Advanced Industrial Science and Technology, volunteer (human), National Institute of Advanced Industrial Science and Technology, Ethical Review Committee, Approval No. 15000-A-20081215-001) and 0.6 mL of an 80 mM phosphoric acid buffer (pH 7.0, containing 4 mM EDTA (ethylenediaminetetraacetic acid)) was introduced onto the above reverse phase column. As washing liquids, the following (i), (ii), and (iii) below were used in sequence for washing.

(i) 2% (v/v) ethanol-containing 10 mM phosphoric acid buffer (pH 7.0): 6.0 mL (ii) 30% (v/v) ethanol-containing 10 mM phosphoric acid buffer (pH 7.0): 4.0 mL (iii) 50% (v/v) ethanol-containing 10 mM phosphoric acid buffer (pH 7.0): 0.8 mL Subsequently, a fraction obtained by passing 0.7 mL of 50% (v/v) ethanol-containing 10 mM phosphoric acid buffer (pH 7.0) was collected as a fraction containing 8-isoprostane. Following this, an SAX manufactured by Varian (ion exchange capacity: 0.8 meq/g, amount of packing 0.5 g, column size 3 mL, column shape syringe type, polypropylene) was prepared as an ion exchange support, and the fraction containing 8-isoprostane collected from the reverse phase support was introduced onto the conditioned SAX. Conditioning of the SAX was carried out by passing ethanol and pure water in that order. The SAX onto which 8-isoprostane had been introduced was washed with 0.4 mL of 50% (v/v) ethanol-containing 10 mM phosphoric acid buffer (pH 7.0), and then a fraction obtained by passing 0.8 mL of 50% (v/v) ethanol-containing 10 mM phosphoric acid buffer (pH 7.0) was collected as a fraction containing 8-isoprostane.

150 µL of this fraction was taken and mixed with 75 µL of Reagent I, 60 µL of Reagent II, and 15 µL of Reagent III, and in the same manner as in Example 1 a treatment by SCX and then an HPLC analysis were carried out.

Example 3

The procedure of Example 2 was repeated except that a urine sample obtained from a different specimen was used.

Figure 3A:
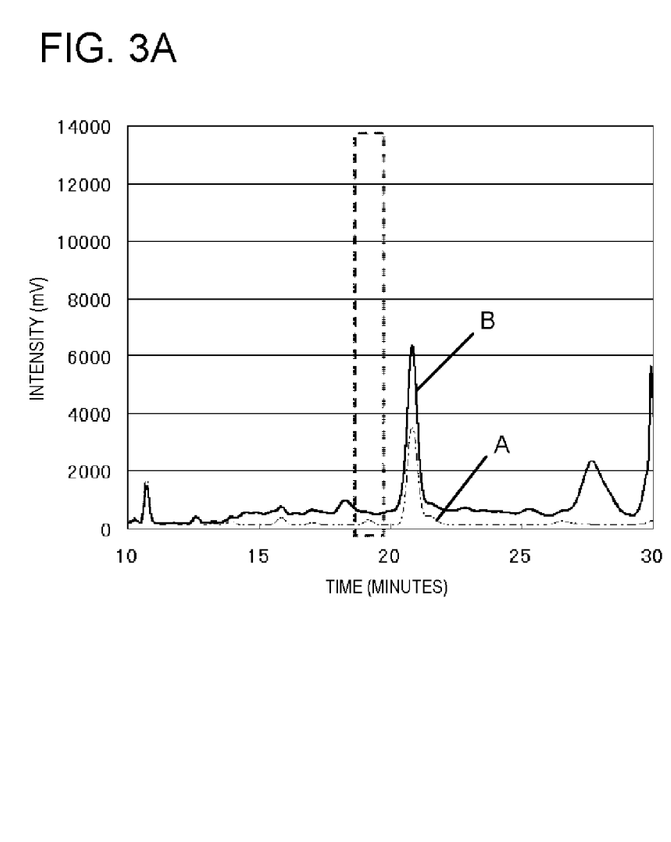
FIGS. 3A and 3B show high-performance liquid chromatography charts obtained in Examples 1 and 2.
Figure 3B:
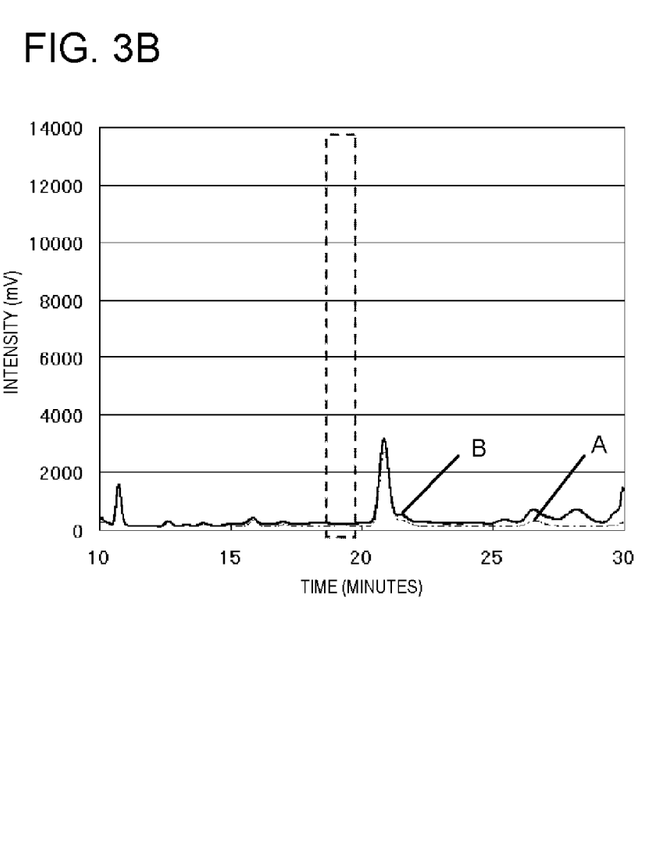
Figure 4A:
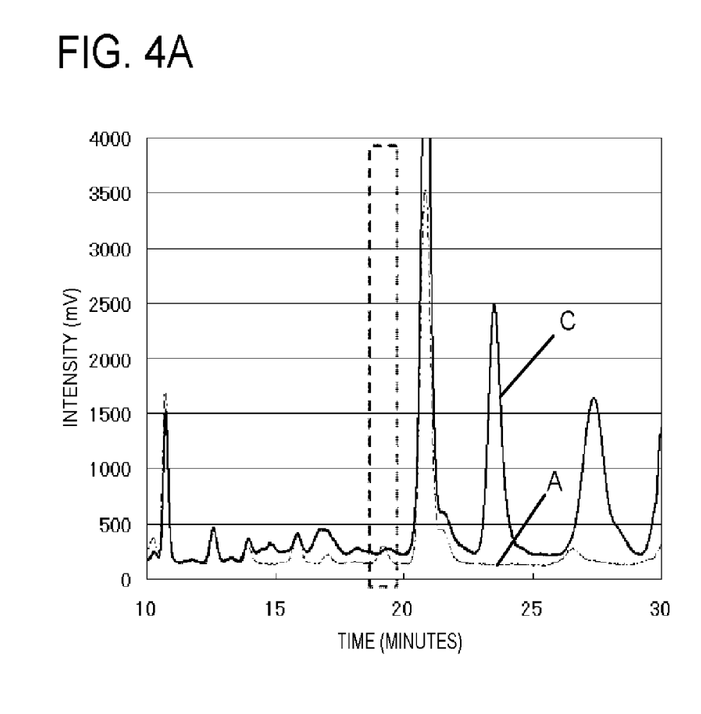
FIGS. 4A and 4B show high-performance liquid chromatography charts obtained in Examples 1 and 3.
Figure 4B:
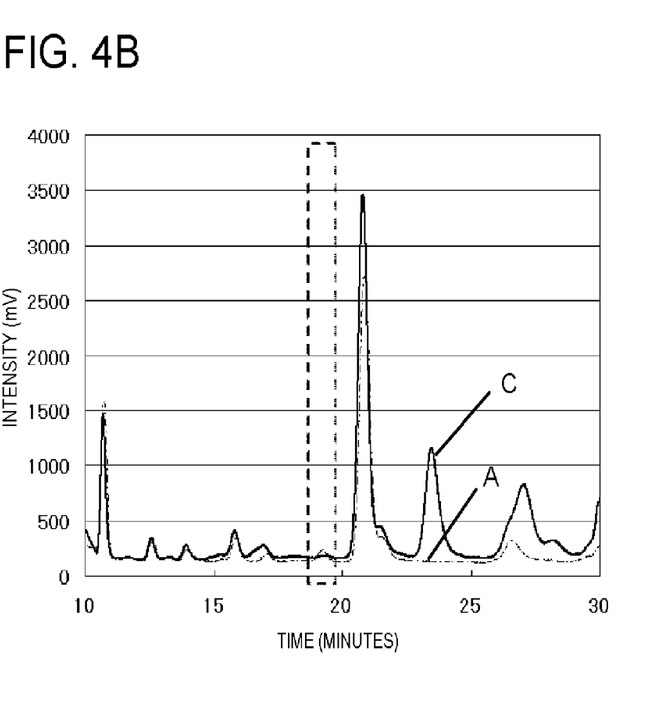

HPLC charts obtained in Examples 1 and 2 are shown in FIGS. 3A and 3B. In FIGS. 3A and 3B, A (broken line) denotes Example 1, and B (solid line) denotes Example 2. Example 2 was carried out twice, B of FIG. 3A shows a chart of the first one of Example 1, and B of FIG. 3B shows a chart of the second one of Example 1. Furthermore, HPLC charts obtained in Examples 1 and 3 are shown in FIGS. 4A and 4B. A (broken line) denotes Example 1, and C (solid line) denotes Example 3. Example 3 was also carried out twice, C of FIG. 4A shows a chart of the first one of Example 3, and C of FIG. 4B shows a chart of the second one of Example 3. In FIGS. 3A, 3B, 4A, and 4B, the retention time for 8-isoprostane is about 19 minutes. In addition, it was confirmed that when a sample of Example 1 was injected at the same time as a sample of Example 2 or 3, peaks at a retention time of about 19 minutes overlapped one another.

With regard to Example 2, preparation was carried out using, instead of urine, 8-isoprostane solutions at 1, 2, 5, 10, 20, and 50 ng/mL, the same procedure was carried out for each thereof, and a calibration curve was produced. The 8-isoprostane solutions were prepared by dissolving an authentic sample (Cayman) of 8-isoprostane in an 8% (v/v) ethanol-containing 10 mM phosphoric acid buffer. Furthermore, with regard to 10 and 50 ng/mL 8-isoprostane solutions, a calibration curve was formed using the average value for n=10, and with regard to 8-isoprostane solutions at 1, 2, 5, and 20 ng/mL, a calibration curve was formed using the average value for n=5. The coefficient of variation was 2.8 to 8.5%. Furthermore, the correlation coefficient of the calibration curve was $R^2=0.9984$.

It was confirmed that in Example 1 when an 8-isoprostane solution was prepared at 2, 4, 10, 20, 40, and 100 ng/mL, a similar calibration curve could be obtained.

From the analytical results of Examples 2 and 3 and the calibration curve thus obtained, it was found that the amount of 8-isoprostane contained in the urine used in Example 2 was 15 pmol/ml, and the amount of 8-isoprostane contained in the urine used in Example 3 was 11 pmol/ml.

It is apparent that the present invention is not limited to the above embodiment, and may be modified and changed without departing from the scope and spirit of the invention.

What is claimed is:

1. A method of quantitatively determining 8-isoprostane, the method comprising:
   fluorescently labeling 8-isoprostane with a quinoxalinone derivative in an excess amount relative to amount by mole of 8-isoprostane, the quinoxalinone derivative which is represented by Formula (1) below (1)

wherein, in Formula (1), $R^1$, $R^2$, and $R^3$ are alkyl groups having 1 to 6 carbon atoms and n is an integer of 0 to 6;
   contacting a reaction mixture containing a fluorescently labeled 8-isoprostane and an unreacted quinoxalinone derivative with a cation exchange support having a sulfonic acid or a sulfonate immobilized thereon to separate the fluorescently labeled 8-isoprostane from the unreacted quinoxalinone derivative, and
   quantitatively determining the fluorescently labeled 8-isoprostane separated from the unreacted quinoxalinone derivative.

2. The method according to claim 1, wherein the quinoxalinone derivative is 1,2,3,4-tetrahydro-6,7-dimethoxy-1-methyl-2(1H)-oxoquinoxaline-3-propionic acid hydrazide.

3. The method according to claim 1, wherein 8-isoprostane is fluorescently labeled using the quinoxalinone derivative at $5\times10^3$ times by mole or more relative to 8-isoprostane, in fluorescently labeling 8-isoprostane.

4. The method according to claim 1, wherein 8-isoprostane is fluorescently labeled by reacting the quinoxaline derivative and 8-isoprostane by heating at 50 to 90° C., in fluorescently labeling 8-isoprostane.

5. The method according to claim 1, wherein fluorescently labeled 8-isoprostane is analyzed using an isocratic high-performance liquid chromatographic method employing a reverse phase column, in said step of quantitatively determining fluorescently labeled 8-isoprostane.

6. The method according to claim 1, wherein the cation exchange support has an alkylbenzenesulfonic acid represented by Formula (2) below or a salt thereof immobilized thereon (2)

wherein, in Formula (2), m is 1 to 6 and $B_1$ is a resin substrate or silica gel.

7. The method according to claim 1, further comprising purifying 8-isoprostane using an anion exchange support,
   wherein fluorescently label 8-isoprostane is carried out using a purified 8-isoprostane.

8. The method according to claim 7, wherein the anion exchange support is an anion exchange support having a quaternary ammonium salt immobilized thereon.

9. The method according to claim 1, further comprising separating 8-isoprostane in a biological sample, wherein fluorescently labeling 8-isoprostane is carried out using a separated 8-isoprostane.

10. The method according to claim 9, wherein the material for the reverse phase support is silica gel having an octadecylsilyl group.

11. The method according to claim 9, wherein the reverse phase support comprises larger medium particles having 35 to 60 μm of a particle size measured by a sedimentation method, and smaller medium particles having 10 to 30 μm of a particle size measured by a Coulter method, and the ratio by weight of the larger medium particles having 35 to 60 μm of the particle size and the smaller medium particles having 10 to 30 μm of the particle size is in the range of 80:20 to 95:5 (the larger medium particles:the smaller medium particles).

12. The method according to claim 9, wherein the biological sample is urine, saliva, or blood.

13. The method according to claim 9, wherein 8-isoprostane is separated from the biological sample by contacting the biological sample with a reverse phase support, in separating 8-isoprostane in a biological sample.

14. The method according to claim 13, wherein the reverse phase support is formed from a material that has a straight-chain hydrocarbon group having 1 to 30 carbon atoms as a functional group and has a carbon content on the support surface of 18% or less as an element ratio.

15. The method according to claim 14, wherein the reverse phase support comprises small particles having 0.5 to 10 μm of an equivalent circle diameter measured by a flow particle image analyzer at 1 to 20 cumulative % as a particle number.

16. The method according to claim 15, wherein the reverse phase support further comprises large particles having 20 to 100 μm of an equivalent circle diameter measured by a flow particle image analyzer at 65 to 99 cumulative % as a particle number.

* * * * *